(12) United States Patent
Vardi et al.

(10) Patent No.: US 10,639,060 B2
(45) Date of Patent: *May 5, 2020

(54) METHOD AND CATHETER FOR CREATING AN INTERATRIAL APERTURE

(71) Applicant: InterShunt Technologies, Inc., St. Louis, MO (US)

(72) Inventors: Gil M. Vardi, Town and country, MO (US); Chris Minar, New Prague, MN (US); Steve Christian, St. Paul, MN (US)

( * ) Notice: Subject to any disclaimer, the term of this patent is extended or adjusted under 35 U.S.C. 154(b) by 228 days.

This patent is subject to a terminal disclaimer.

(21) Appl. No.: 15/812,815

(22) Filed: Nov. 14, 2017

(65) Prior Publication Data

US 2018/0064460 A1 Mar. 8, 2018

Related U.S. Application Data

(63) Continuation of application No. 14/738,802, filed on Jun. 12, 2015, now Pat. No. 9,814,483.

(Continued)

(51) Int. Cl.
*A61B 17/3205* (2006.01)
*A61B 17/32* (2006.01)
(Continued)

(52) U.S. Cl.
CPC .. *A61B 17/3205* (2013.01); *A61B 17/320016* (2013.01); *A61B 17/32053* (2013.01); *A61B 17/3478* (2013.01); *A61B 2017/00247* (2013.01); *A61B 2017/22042* (2013.01); *A61B 2017/22047* (2013.01); *A61B 2017/22069* (2013.01); *A61B 2017/306* (2013.01); *A61B 2017/320064* (2013.01); *A61B 2017/3458* (2013.01)

(58) Field of Classification Search
CPC ............ A61B 17/32; A61B 17/320016; A61B 17/3205; A61B 17/32053; A61B 2017/00247; A61B 2017/00252; A61B 2017/003; A61B 2017/00318; A61B 2017/00323; A61B 2017/32004; A61B 2017/320056; A61B 2017/320064

See application file for complete search history.

(56) References Cited

U.S. PATENT DOCUMENTS 4,018,228 A 4/1977 Goosen
5,702,412 A 12/1997 Popov et al.
(Continued)

FOREIGN PATENT DOCUMENTS

WO WO 02/47561 A1 6/2002

OTHER PUBLICATIONS

Barry A. Borlaug, The sHunt for better breathing in heart failure with preserved ejection fraction, European Journal of Heart Failure, 2014, 709-11, vol. 16.

(Continued)

*Primary Examiner* — Ryan J. Severson
(74) *Attorney, Agent, or Firm* — John M. Berns (57) ABSTRACT

A catheter device with a cutting structure or means on the distal portion is disclosed, along with a medical procedure for using the device. The catheter is utilized in such a way as to create a permanent interatrial aperture in the heart, including creating a permanent interatrial hole and/or removing tissue.

18 Claims, 10 Drawing Sheets

Related U.S. Application Data (60) Provisional application No. 62/012,212, filed on Jun. 13, 2014.

(51) Int. Cl.
*A61B 17/34* (2006.01)
*A61B 17/22* (2006.01)
*A61B 17/00* (2006.01)
*A61B 17/30* (2006.01)

(56) References Cited

U.S. PATENT DOCUMENTS

| | | | |
|---|---|---|---|
| 5,893,369 | A | 4/1999 | LeMole |
| 5,910,153 | A | 6/1999 | Mayenberger |
| 6,022,367 | A | 2/2000 | Sherts |
| 6,080,173 | A | 6/2000 | Williamson et al. |
| 6,428,555 | B1 | 8/2002 | Koster, Jr. |
| 6,468,227 | B2 | 10/2002 | Zimmon |
| 6,626,921 | B2 | 9/2003 | Blatter et al. |
| 6,695,859 | B1 | 2/2004 | Golden et al. |
| 6,743,244 | B2 | 6/2004 | Blatter et al. |
| 6,863,677 | B2 | 3/2005 | Breznock |
| 6,893,449 | B2 | 5/2005 | Vargas et al. |
| 7,056,294 | B2 | 6/2006 | Khairkhahan et al. |
| 7,144,405 | B2 | 12/2006 | Vargas et al. |
| 7,771,442 | B2 | 8/2010 | Shriver |
| 7,799,041 | B2 | 9/2010 | Beane et al. |
| 8,043,360 | B2 | 10/2011 | McNamara et al. |
| 8,070,708 | B2 | 12/2011 | Rottenberg et al. |
| 8,091,556 | B2 | 1/2012 | Keren et al. |
| 8,157,860 | B2 | 4/2012 | McNamara et al. |
| 8,172,896 | B2 | 5/2012 | McNamara et al. |
| 8,216,265 | B2 | 7/2012 | Haunschild et al. |
| 8,226,670 | B2 * | 7/2012 | Beane ............... A61B 17/0218 606/153 |
| 8,235,933 | B2 | 8/2012 | Keren et al. |
| 8,252,042 | B2 | 8/2012 | McNamara et al. |
| 8,328,751 | B2 | 12/2012 | Keren et al. |
| 8,460,372 | B2 | 6/2013 | McNamara et al. |
| 8,597,315 | B2 | 12/2013 | Snow et al. |
| 8,696,611 | B2 | 4/2014 | Nitzan et al. |
| 8,740,962 | B2 | 6/2014 | Finch et al. |
| 8,745,845 | B2 | 6/2014 | Finch et al. |
| 8,752,258 | B2 | 6/2014 | Finch et al. |
| 8,771,302 | B2 | 7/2014 | Woolfson et al. |
| 8,771,305 | B2 | 7/2014 | Shriver |
| 8,882,697 | B2 | 11/2014 | Celermajer et al. |
| 8,951,223 | B2 | 2/2015 | McNamara et al. |
| 8,956,377 | B2 | 2/2015 | Khalapyan |
| 9,005,155 | B2 | 4/2015 | Sugimoto |
| 9,034,034 | B2 | 5/2015 | Nitzan et al. |
| 9,205,236 | B2 | 12/2015 | McNamara et al. |
| 9,232,997 | B2 | 1/2016 | Sugimoto et al. |
| 9,277,995 | B2 | 3/2016 | Celermajer et al. |
| 9,358,371 | B2 | 6/2016 | McNamara et al. |
| 9,629,715 | B2 | 4/2017 | Nitzan et al. |
| 9,642,993 | B2 | 5/2017 | McNamara et al. |
| 9,649,480 | B2 | 5/2017 | Sugimoto et al. |
| 9,707,382 | B2 | 7/2017 | Nitzan et al. |
| 9,713,696 | B2 | 7/2017 | Yacoby et al. |
| 9,724,499 | B2 | 8/2017 | Rottenberg et al. |
| 9,757,107 | B2 | 9/2017 | McNamara et al. |
| 9,775,636 | B2 | 10/2017 | Fazio et al. |
| 9,814,483 | B2 * | 11/2017 | Vardi ............... A61B 17/3205 |
| 9,943,670 | B2 | 4/2018 | Keren et al. |
| 9,980,815 | B2 | 5/2018 | Nitzan et al. |
| 10,045,766 | B2 | 8/2018 | McNamara et al. |
| 10,188,375 | B2 | 1/2019 | McNamara et al. |
| 2002/0169377 | A1 * | 11/2002 | Khairkhahan ....... A61B 5/0084 600/433 |
| 2006/0009715 | A1 | 1/2006 | Khairkhahan et al. |
| 2006/0111733 | A1 * | 5/2006 | Shriver ................ A61F 2/06 606/153 |
| 2007/0185513 | A1 * | 8/2007 | Woolfson ......... A61B 17/32002 606/108 |
| 2010/0010500 | A1 | 1/2010 | Beane |
| 2010/0057192 | A1 | 3/2010 | Celermajer |
| 2010/0121258 | A1 * | 5/2010 | Shriver ......... A61B 17/320758 604/22 |
| 2010/0298850 | A1 * | 11/2010 | Snow ............. A61B 17/32075 606/159 |
| 2011/0071623 | A1 | 3/2011 | Finch et al. |
| 2011/0218480 | A1 | 9/2011 | Rottenberg et al. |
| 2011/0218481 | A1 | 9/2011 | Rottenberg et al. |
| 2011/0270239 | A1 | 11/2011 | Werneth |
| 2011/0295183 | A1 | 12/2011 | Finch et al. |
| 2012/0259263 | A1 * | 10/2012 | Celermajer ........ A61B 18/1492 604/8 |
| 2012/0265296 | A1 | 10/2012 | McNamara et al. |
| 2012/0289882 | A1 | 11/2012 | McNamara et al. |
| 2012/0290062 | A1 | 11/2012 | McNamara et al. |
| 2013/0006281 | A1 | 1/2013 | Golden et al. |
| 2013/0178784 | A1 | 7/2013 | McNamara et al. |
| 2013/0218261 | A1 | 8/2013 | Beane |
| 2013/0267885 | A1 | 10/2013 | Celermajer et al. |
| 2013/0281988 | A1 | 10/2013 | Magnin et al. |
| 2014/0128795 | A1 | 5/2014 | Keren et al. |
| 2014/0128796 | A1 | 5/2014 | Keren et al. |
| 2014/0163449 | A1 | 6/2014 | Rottenberg et al. |
| 2014/0194971 | A1 | 7/2014 | McNamara |
| 2014/0277039 | A1 | 9/2014 | Liberatore et al. |
| 2014/0277043 | A1 | 9/2014 | Jenkins et al. |
| 2014/0277054 | A1 | 9/2014 | McNamara et al. |
| 2015/0359556 | A1 * | 12/2015 | Vardi ................ A61B 17/3205 606/170 |
| 2016/0270810 | A1 * | 9/2016 | Vardi ................ A61B 17/3205 |
| 2018/0064460 | A1 * | 3/2018 | Vardi ................ A61B 17/3205 |
| 2018/0177516 | A1 * | 6/2018 | Vardi ................... A61B 34/73 |
| 2019/0029705 | A1 * | 1/2019 | Vardi ................ A61B 17/3205 |

OTHER PUBLICATIONS

Michael A. Burke et al., Prognostic Importance of Pathophysiologic Markers in Patients With Heart Failure and Preserved Ejection Fraction, Circulation, Heart Failure, Dec. 23, 2013, 288-299, vol. 7.

Rainer Hoffmann, et al., Functional Effect of New Atrial Septal Defect After Percutaneous Mitral Valve Repair Using the MitraClip Device, Am J Cardiol, 2014: 113:1228-1233.

Lourdes R. Prieto, et al., Atrial Septostomy Using a Butterfly Stent in a Patient With Severe Pulmonary Arterial Hypertension, Catheterization and Cardiovascular Interventions, Sep. 12, 2006, 68:642-647.

Paul M. Seib, et al., Blade and Balloon Atrial Septostomy for Left Heart Decompression in Patients with Severe Ventricular Dysfunction on Extracorporeal Membrane Oxygenation, Catheterization and Cardiovascular Interventions, 1999, 46:179-186.

Lars Sondergaard et al., Transcatheter Treatment of Heart Failure with Preserved or Mildly Reduced Ejection Fraction Using a Novel Interatrial Implant to Lower Left Atrial Pressure, European Journal of Heart Failure, Jun. 24, 2014, 16:796-801.

Ignacio J. Amat-Santos et al., Left Atrial Decompression Through Unidirectional Left-to-Right Interatrial Shunt for the Treatment of Left Heart Failure: First-In-Man Experience with the new V-Wave Device, EuroIntervention, May 2014.

David Kaye, et al., Effects of an Interatrial Shunt on Rest and Exercise Hemodynaics: Results of a Computer Simulation in Heart Failure, Journal of Cardiac Failure, 2014, 20:3:212-21.

* cited by examiner

METHOD AND CATHETER FOR CREATING AN INTERATRIAL APERTURE

CROSS REFERENCE TO RELATED APPLICATIONS

This application claims the benefit of priority to U.S. patent application Ser. No. 14/738,802, filed Jun. 12, 2015, now U.S. Pat. No. 9,814,483, which claims priority to U.S. Provisional Application No. 62/012,212 filed Jun. 13, 2014, the entire disclosures of which are hereby incorporated by reference.

BACKGROUND OF THE INVENTION

Field of the Invention

The invention relates to medical devices and methods of medical treatment. The invention relates to a medical device and method of treatment used to create an aperture in the interatrial septum of a heart.

Background Art

There are some medical conditions that are treated by creating an opening between body chambers in order to create a connection between the chambers. The heart has an interatrial septum or wall that separates the left atrium and the right atrium. In certain heart failure patients (e.g., heart failure with preserved ejection fraction (diastolic dysfunction)) there is a need to allow blood flow from the left atrium to the right atrium to reduce left atrial pressure. Likewise, certain other heart diseases and conditions, such as congenital heart diseases and pulmonary hypertensions may require a similar treatment. Implanting a stent in the interatrial septum has been used as a treatment for elevated pressure in one atrium by allowing blood to flow through the opening to the other atrium to reduce blood pressure. A heart surgeon implants the stents in certain predetermined sizes in an effort to control the amount of blood flow between the atria.

One procedure uses a balloon to create a hole in the septum. However, it has been found that a hole created in this manner may not stay open and after a period of time may spontaneously close. This renders this particular therapeutic solution temporary.

A few other devices have been proposed in order to overcome the temporary solution of using a balloon. One device is to use a stent to keep the hole open. Another device uses a valve inserted into the septum that keeps the hole open and also assists in controlling blood flow. Significant drawbacks to these devices are that they are permanent implants that can promote thrombosis and are potentially subject to infection.

Another major drawback of these devices is that they are not capable of removing a segment of the septum. The benefit of removing a segment of the septum is that hole will be less likely to close spontaneously. The stents may also become spontaneously dislodged and embolize and cause cardiac damage or blockage of blood flow.

Therefore, it would be desirable to have a medical device that is capable of creating an incision or an opening in the interatrial septum of the heart to alleviate pressure between chambers in the heart that does not suffer from the limitations of prior devices or procedures. It would be advantageous to have a catheter that can create various slits, openings, or apertures in the interatrial septum in a predetermined orientation. It would also be advantageous to have a catheter that may be easily manipulated to remove a section of the interatrial septum to form a permanent hole that is less likely to spontaneously close.

BRIEF SUMMARY OF THE INVENTION

The present invention solves these needs by providing a medical device that includes a catheter, a cutting blade, and a tissue articulator and a method of providing a durable interatrial shunt.

In one embodiment, the medical device includes a catheter with a catheter shaft that has a central lumen and a distal catheter lumen. The catheter also has a shaped blade around the distal catheter lumen. The blade is adapted to cut an area of tissue to create an aperture in a tissue. The catheter also has a tissue articulator, the tissue articulator having a first position and a second position, is configured to move with respect to the shaped blade, and is adapted to hold the tissue against the shaped blade for cutting while in the second position. The catheter also includes an actuator connected to the tissue articulator, the actuator having a first position and a second position, wherein when the actuator is in the second position the tissue articulator holds the tissue against the shaped blade.

In another embodiment the invention is a method of treating congestive heart failure including the steps of inserting a catheter into the right atrium of the heart, the catheter including a shaft, a shaped cutting blade, a tissue articulator, the tissue articulator having a first position and a second position, an actuator connected to the tissue articulator. The embodiment further includes the steps of crossing the interatrial septum, actuating the actuator to move the tissue articulator into a second position that holds the tissue against the shaped cutting blade, cutting an aperture in the interatrial septum between the right atrium and the left atrium, removing a cut tissue from the right atrium.

In one embodiment the method further includes a step of attaching a tissue removal device to the interatrial septum. The tissue removal device may be actuated to remove the cut tissue. It may comprise a hook, a balloon, a disk, or an expandable basket. The tissue removal device may tent the tissue to pull, grasp, or push the tissue into a catheter lumen or the shaped blade.

In another the method further includes a step of pulling the attached tissue into a lumen at a distal end of the catheter shaft. The method may also include a step of expanding the cutting device to a diameter greater than the diameter of the catheter.

In another embodiment, the tissue removal device has a proximal portion and a distal portion, and the method further includes the step of actuating the tissue removal device. Actuating the tissue removal device can reduce the distance between the proximal portion and distal portion of the tissue removal device. Actuating the tissue removal device can cause the proximal portion and the distal portion of the tissue removal device to securely hold the tissue between them.

The removing step can include a step of withdrawing the tissue removal device into the shaped blade or the catheter with the cut tissue.

In one embodiment the method includes the step of aligning the tissue and the shaped cutting blade so they are substantially parallel. In another, the removing step comprises pulling the cut tissue into a lumen at a distal end of the catheter shaft. In one embodiment the method further includes a step of applying suction to the tissue. In another, the method further comprises the step of tenting the tissue so that a larger portion of the tissue may be cut in the cutting step. In one aspect of this embodiment, the tissue articulator is a tapered cone having a proximal face, and the tenting step uses the proximal face to pull the tissue into the catheter to tent the tissue.

In another embodiment, the method further comprises the step of locating a radiopaque marker on the catheter. In another aspect, the method further comprises the steps of inserting the catheter in a sheath, navigating the sheath to the heart, and advancing a distal part of the catheter out of the sheath. The method may include the further step of locating a radiopaque marker on the sheath.

DETAILED DESCRIPTION OF THE PREFERRED EMBODIMENTS

In general, the invention comprises a medical procedure and corresponding medical devices for therapeutic surgical procedures. In particular, the invention comprises a method of treating heart failure with by creating an aperture between body chambers in order to create blood flow between the chambers and a device for doing so. In this context, an aperture is a created space or gap large enough to allow significant blood flow between the two chambers it connects, without the use of an implanted device.

In order to treat congestive heart failure, it must first be diagnosed. In particular diagnosis may comprise listening to the lungs for signs of congestion, a chest x-ray of the lungs, ECG, an ultrasound, a blood test, e.g., to check for a chemical called N-terminal pro-B-type natriuretic peptide (NT-proBNP), a stress test and/or an MRI or CT scan. In addition, an ultrasound may be used to confirm the absence of any current holes between the chambers of the heart.

Once congestive heart failure is diagnosed a course of treatment will be designed. While it is possible to treat congestive heart failure with surgery, implants, or other methods, herein disclosed is a method of advantageously treating congestive heart failure without surgery and without leaving behind an implant.

The disclosed procedure preferably begins with a percutaneous entry into a vein, preferably the femoral vein in the groin region. It is also possible to gain entry via a jugular vein or neck vein. Typically a sheath with a guide wire is inserted through the percutaneous entry and maneuvered by the physician to the right atrial chamber. The sheath may be steerable, for example controlled by pull wires which extend from its distal region to a handle at its proximal end, the handle having one or more actuators. Likewise the sheath may be pre-curved such that it will automatically orient towards the interatrial septum once it reaches the right atrium.

Once in the right atrium, the physician will identify the portion of the interatrial septum at which he desires to cross into the left atrium, or at which he will create the interatrial aperture. Typically, this will be at the fossa ovalis. Because the fossa ovalis is thinner than the remainder of the interatrial septum, it will be easiest to cut an aperture at its location. To identify the fossa ovalis the physician may employ one or more means of tissue thickness sensing. For example the physician may use an electrode and test for impedance changes, may employ one or more ultrasound methods, or may simply test for tenting. For example, the physician may apply a small amount of pressure to the interatrial septum and search for tenting in the tissue. Once the physician locates the spot where the tissue easily tents, e.g. the fossa ovalis, the physician will cross into the left atrium. The physician will create a small puncture in the septum using a transseptal device. For example a brockenbrough needle, a BRK needle, or another transseptal device may be used for crossing the septum into the left atrium. Once there, the guidewire is threaded through the interatrial septum puncture and the distal end of the guidewire is left in the left atrium. The proximal end of the guidewire will remain outside of the body, with its entry point at the femoral vein.

Depending on the therapeutic catheter that will be used in the latter portion of this procedure it is possible that a guidewire may not be required. In such instances a transseptal device may not be necessary either. If the catheter to be used to form the interatrial aperture is designed to create its own transseptal crossing or create an aperture without crossing the septum, the guidewire or transseptal device may be avoided, potentially saving cost and time.

With the guidewire in place, the sheath may be removed. If so, a surgical catheter and/or a sheath will be provided and directed over the guidewire into the right atrium. Once there the therapy catheter, further to the surgical mechanisms disclosed in detail below, will create a durable interatrial aperture.

During the procedure the physician will monitor the location of the catheter and/or sheath as well as the progress of the cut, the nature of the aperture, or other procedure details via fluoroscopy, MRI, ultrasound, or transesophageal echocardiography, intracardiac echocardiography (ICE) or similar tracking or visualization technology for guidance. Toward this end, it is preferred that the catheter includes radiopaque or ultrasound markers as described in further detail below. Likewise, the physician may monitor the location of the catheter and/or sheath as well as the progress of the cut, the nature of the aperture, or other procedure details via a camera, such as a CCD camera. In the latter case it may be advantageous to apply a hood over the operation region, empty the hood of blood and replace it with saline, such that the procedure may be visually monitored.

The interatrial aperture will be created by one of two mechanisms or a combination thereof. First the surgical catheter will use a cutting blade to create an aperture or cut pattern in the interatrial septum such that a sufficient flow of blood may occur between the two atria. For example, the catheter may cut an X—pattern aperture in the septum. Doing so leaves flaps that will open and close depending on the pressure differential between the two atria. Likewise the catheter may create a circular or semi-circular hole in the septum.

Second the catheter may remove tissue. For example in creating a shaped aperture the catheter may utilize a cutting blade to cut the tissue from the septum and remove it from the body. Loose tissue removal is critical so that any loose tissue does not remain in the atria, creating a substantial risk of stroke due to embolization.

In either mechanism, the physician preferably engages the target tissue with a distal portion of the device, such as a tissue articulator. The tissue articulator may penetrate into or through the tissue, and then be actuated (e.g., via an actuator on the catheter or sheath handle) to hold the tissue against the cutting blade. Thus, the articulator works with the blade for one or more purposes, it may hold the tissue in place, guide the blade to the desired portion of the tissue, hold the catheter in place and on target, retain any loose tissue, or create an initial opening in the tissue for the device to pass into.

In a preferred embodiment, the tissue articulator passes through the tissue as the catheter or sheath is advanced. Alternatively, an actuator, (e.g., an actuator on a handle, or simply a movable lumen/guide within the medical device) may be in or moved to a first position that advances or locates the tissue articulator forward away from the cutting blade. This advancement may push the tissue articulator through the tissue. Once the tissue articulator is in place, either by actuation or mere advancement, the actuator is activated to a second position that causes it to engage the tissue. The second position (or a third position) may also pull the tissue into a lumen in the catheter or sheath, tenting it so that a larger aperture may be cut.

It is critical that the aperture be "durable" such that it will stay open for a long period of time and even permanently, as defined below. It is preferred that the hole be at least 4 to 10 mm, or 6 to 8 mm, in diameter for a standard patient for the desired clinical benefit. The clinically necessary size will vary from patient to patient. Subsequent to the procedure the physician will monitor the patient at one month, three-month, and six-month exams to determine if the size of the hole has shrunk. While it is anticipated that healing tissue may slightly shrink the aperture on the order of 1 to 2 mm, if the aperture remains open at six months it is considered "permanent" for purposes herein. It is also desirable that the aperture be visible on an echocardiogram so that it can be readily measured.

The tissue may be removed by a device using, for example, suction or grasping mechanisms. In a preferred embodiment the catheter, e.g., the tissue articulator, will pull the tissue into the blade to positively retain it and keep it from releasing into the heart. In addition to its utility for tissue removal, the suction and grasping mechanisms may also be extremely useful for positioning the device, and retaining the device in the desired position during operation.

Creating a hole in the heart without leaving behind an implant avoids the need for anticoagulant therapy, lowers the risk of infection, and avoids the use of an implant that may come loose over time. In addition the procedure is substantially simpler than leaving behind an implant. Due to the lack of an implant, there are no risks of MRI compatibility, no risk of device failure or fracture. It is easier to close the aperture if needed absent a device, and the overall total cost of care is lower. Finally, the procedure is faster and will allow for a more efficient use of hospital facilities and physician time.

There are multiple ways to determine if the aperture is large enough to be efficacious. Subsequent to the procedure the physician do so by, e.g., examining the aperture on an echocardiogram, calculating the degree of shunting, performing an exercise tolerance procedure, by measuring the ejection fraction, by measuring the wedge pressure, oxygen saturation, or other means. It is preferred that a clinical evaluation be conducted such as a walking test, to determine the practical effect on the patient. The invention allows for easier adjustment of aperture size compared to similar solutions.

Also disclosed is a medical device for creating the aperture between the left atrial chamber and the right atrial chamber. The medical devices have dimensional requirements depending on several factors. First, the length of the device will depend on its point of entry. For example, a catheter that will be used in a percutaneous entry at the femoral vein and which must reach to the right atrium will typically be at least 120 cm long and more preferably 140 cm. A catheter that will enter the body at a different location in many cases will be substantially shorter. The more lengthy and torturous the path the catheter must take, the stiffer the catheter body may need to be, and the more likely the catheter will be to require stiffening elements such as a stainless steel or nitinol braid. Typically a thinner catheter is preferred, so long as the cutting elements are sufficiently sized to create a large enough interatrial aperture. For example, it would be preferred to have a catheter shaft of nine French however there is always a trade-off between a small diameter device and the need to create a sufficiently sized interatrial aperture. Thus it may be advantageous to have a small diameter shaft for the bulk of the catheter length combined with a somewhat larger distal working end on the catheter or an expandable distal working end that has a small diameter upon insertion to the vein and can be expanded once in the right atrium and then collapse back to a smaller diameter for removal through the vein. On the proximal end of the catheter it is advantageous to have an easily manipulable handle so that the physician can direct the catheter into its desired location and control the cutting device.

Figure 1:
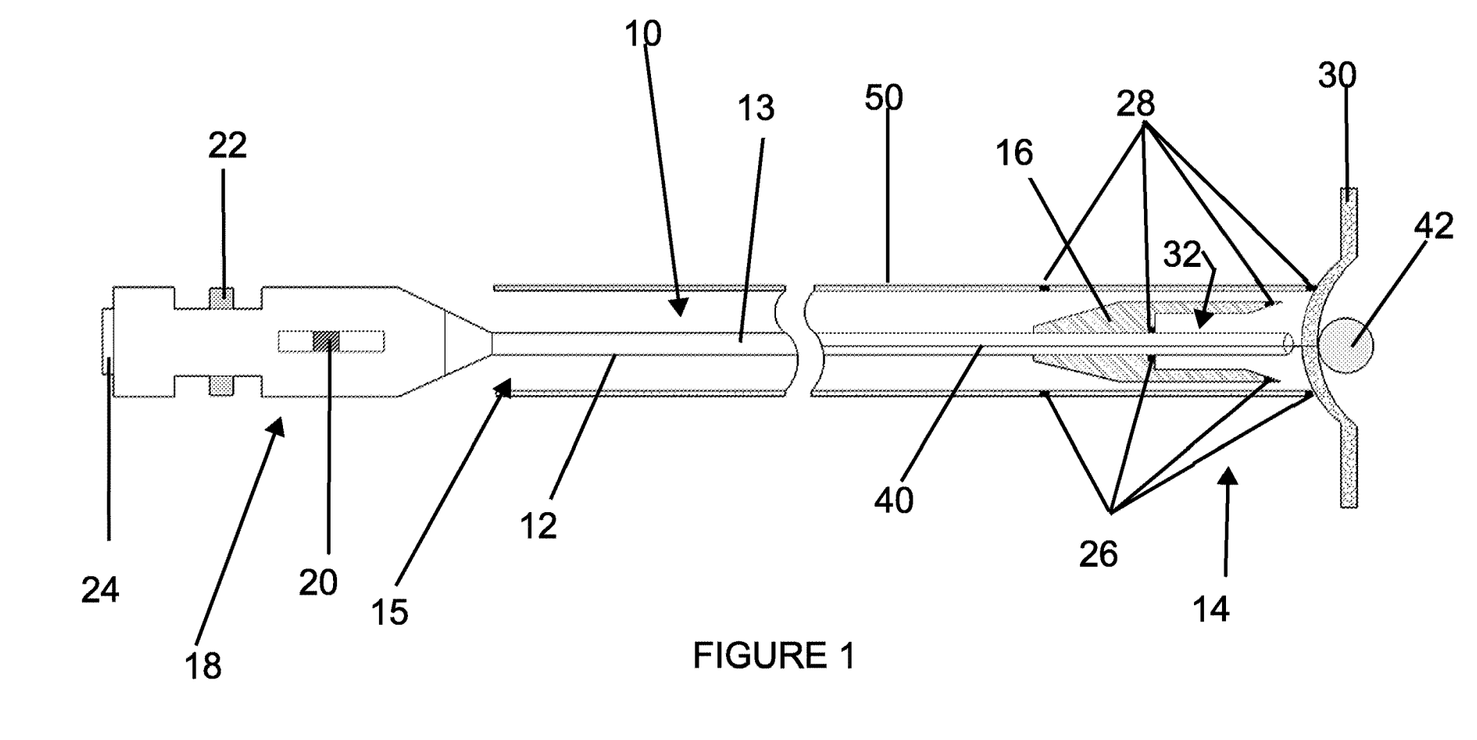
FIG. 1 is a partial perspective view of a catheter constructed according to the present disclosure.

With reference to FIG. 1, the catheter 10 comprises an elongated catheter shaft 12 having a distal end 14 and a proximal end 15. Proximal end 15 includes a handle 18. The handle 18 comprises a first actuator 20 and a second actuator 22. Handle 18 further includes a fluid port 24 and an electrical connection (not shown). Catheter 10 may further include pull wires attached to an actuator for actuating distal elements, moving a lumen or shaft, steering, or the like. It may further include irrigation ports and the like. Catheter 10 further includes radiopaque markers 26 in a designed pattern that allows the physician to determine the location and orientation of the catheter 10 in the patient and the orientation of the different components of the device relatively to each other. Catheter 10 may further include ultrasound markers 28 again in a designed pattern such that the physician may locate the catheter 10 in the patient on ultrasound imaging.

The elongated catheter shaft 12 is preferably hollow, having a lumen 13 that has the ability to pass a guidewire 40 through it. Catheter 10 is designed to work in conjunction with an introducer 50. Introducer 50 may either extend the entire length from the percutaneous incision to the left atrium of the heart, or may only cover a portion of catheter 10.

The distal end 14 of catheter 10 comprises a cutting means 16. In a first embodiment the cutting means 16 is a razor like member formed of steel or another suitable metal or material adapted to cut a thin tissue. Toward this end the cutting means may be very thin so that it cleanly and easily pierces the thin tissue. In those embodiments where cutting means 16 has a sharp edge exposed at the end of the catheter 10, it is it is preferred that the introducer 50 cover and protect the vein and other tissue from the cutting means 16 until the catheter 10 is delivered in place and actuated by the physician to cut the target tissue. In other embodiments a cone (not pictured) or other distal element may sit flush with the cutting blade 16 so that the blade is protected until actuation.

The cutting means 16 may be a serrated blade which will allow for a lower cutting force. Likewise the cutting means 16 may comprise a vibrating blade to likewise allow for a lower cutting force.

The introducer 50 is typically a hollow sheath. Introducer 50 may include braiding along the outer cylinder to provide stiffening. Introducer 50 may further include a handle at the proximal end, an actuator, pull wires attached to the actuator for steering, irrigation ports and the like. In particular, pull wires may be strongly advantageous. Unlike prior art devices which create a hole by energy sources or by implanting a device, the present device may find that significant pressure is necessary on the cutting blade 16. Because the pressure must be transmitted from the length of the introducer or catheter, that pressure will initially push the cutting edge and the entire catheter upwards rather than towards the left atrium. Providing stability and steerability in either the introducer or the catheter may greatly reduce this upward pressure and redirect the force towards the interatrial septum 30 to provide a proper cut.

Introducer 50 further includes radiopaque markers 26 in a designed pattern that allows the physician to determine the location and orientation of the introducer 50 in the patient. Introducer 50 may further include ultrasound markers 28 again in a designed pattern such that the physician may locate the introducer 50 in the patient on ultrasound imaging. Preferably, the radiopaque markers 26 and ultrasound markers 28 on the catheter and introducer are distinguishable from each other and accordingly the physician is able to determine which markers are on the catheter in which markers are on the introducer readily such that the physician is able to determine the spatial relationship of the two devices, the catheter 10 and the introducer 50.

This spatial relationship allows the physician is to determine when the catheter 10 exits the introducer 50 and the cutting mechanism 16 is active, as well as determine the location and orientations of the devices at all times.

Ideally, in operation the introducer 50 is positioned next to or near a target tissue 30. Specifically the introducer 50 is located near the interatrial septum. The introducer 50 may be so located through a physician's experience touch and feel, or using the markers 26, 28 in conjunction with imaging system. Other location systems are possible, including MRI, electroanatomical navigation systems such as EnSite®, Carto®, or MediGuide® systems, along with the corresponding sensors on the introducer 50 and catheter 10.

Once the introducer is located next to or near the target tissue 30 the catheter 10 is advanced past the end of or to the end of the introducer 50 and placed in contact with the tissue 30. Preferably using the unique markers 26, 28 the physician can tell on the visualization system when the catheter has exited the introducer. In a first embodiment, the circular cutter 16 is advanced into the tissue 30 to cut a circular aperture in the tissue. In an alternative embodiment the introducer 50 is not utilized and the catheter itself is steered into position near tissue 30, and is advanced to cut the aperture.

In one embodiment, once the introducer is in place a transeptal crossing system is used to cross the fossa. Then once across the crossing system is typically replaced with a guidewire. The guidewire 40 remains in position across the interatrial septum and guides either the introducer 50 or the catheter 10 into position. Guidewire 40 may comprise a retention means on its distal end. Alternatively, guidewire 40 or the retention means may be a part of catheter 10. For example guidewire 40 may include a balloon 42, a pigtail (not shown), an expandable nitinol basket (not shown) or similar means. In operation the guidewire 40 is passed through the interatrial septum. Once across, balloon 42 is inflated (or the pigtail secured or the nitinol basket expanded) and the guidewire is pulled proximally towards catheter 10 to secure the tissue against catheter 10 and cutter 16. Likewise a pigtail, hook or helical means can be utilized to secure the tissue against catheter 10. Multiple means may be used, including a balloon 42 to push the tissue and a hook to retain any loose or dislodged tissue.

While the balloon, pigtail, or similar means are shown as being on the distal portion of guidewire 40, they may also be on the distal portion of the catheter 10. For example a thinner, distal portion of catheter 10 may be passed through the interatrial septum 30 to allow the balloon 42, or pigtail 44 to secure the tissue 30. The distal portion of the catheter with the balloon 42 or pigtail 44 may ride over a guidewire, or may forego a guidewire entirely. In such an embodiment the catheter 10 may not need lumen 13, or may find alternative usage for it, such as irrigation or suction. Of course a lumen 13 for a guidewire 40 may still use the lumen 13 for irrigation and suction as well.

In an embodiment the balloon 42 or pigtail will pull the tissue of the interatrial septum into a lumen 32 of catheter 10 such that the tissue is tented into the catheter's lumen (as shown). Once the tissue is tented the cutter 16 will cut the tissue 30 resulting in a larger aperture due to the tenting. Tenting the tissue has several advantages. First in many cases it will allow for a larger aperture size. Likewise it may give the physician a degree of control over the size the aperture. For example if the physician desires a smaller aperture for a particular patient, he may wish to reduce the amount of tenting or keep it to a minimum. If the physician desires a larger aperture for the patient he will increase the amount of tenting pulling the tissue further into the lumen 32 creating a larger aperture when the cutting means 16 is applied.

While the above description describes guidewire 40 as a separate device, it is also contemplated that catheter 10 may comprise a lumen in its center filled by the guidewire 40. In this embodiment guidewire 40 is first advanced across the interatrial septum, either by itself, piercing the septum, or over a pre-existing guidewire placed earlier in the procedure. The guidewire 40 may be actuated by the first or second actuator 20, 22 on handle 11, manually by the physician, or by an actuator on a separate handle.

In one embodiment the handle 11 comprises a sliding actuator that advances the guidewire distally or withdraws it approximately in a one-to-one ratio between the movement of the guidewire and the movement of the actuator on the handle. In this situation once the catheter is advanced to the interatrial septum and the guidewire 40 is advanced across the septum, the balloon is inflated, and pulled back against the tissue 30 by actuation or by withdrawing the entire device. At this point the actuator 20 is moved proximally to pull the tissue into the cutter 16 creating the aperture in the tissue 30.

Because the guidewire may include a pigtail or hook, the tissue cut from the interatrial septum to complete the aperture is positively retained the inside the catheter 10 and is withdrawn from the body with the catheter 10. While the guidewire has been described as having either a balloon or pigtail, other tissue retention devices are contemplated. In particular a disc device can be utilized (not shown). The disc device may include one disc that is navigated to the distal side of tissue 30, or may include a disc on each side of the tissue 30. The two discs may be actuated to secure the tissue between them. The disc may be expandable having a small diameter when crossing the septum and a larger diameter when securing the tissue. Cutter 16 may ride over the discs, pulling them into lumen 32, to cut the tissue which then remains retained between the two discs and is removed from the body.

After the tissue 30 is cut the balloon 42 is deflated and it is retracted back into the catheter 10. Likewise, if the device utilizes a pigtail or discs they are withdrawn into the catheter after the tissue is cut. Likewise catheter 10 may utilize a suction device (not shown) to remove any tissue that is cut or loosened from the atrial septum.

The cutter 16 is preferably a shaped blade 16 located around the distal catheter lumen 32. In a first embodiment, shaped blade 16 is circular in shape and has on its distal end a razor like member formed of steel or another suitable metal or material. In a related embodiment the cutter 16 includes saw teeth for cutting through the tissue 30. In another embodiment cutter 16 comprises rotary blade 16 and is capable of spinning or rotating to cut or form an incision. The rotary blade 16 may comprise a blade capable of spinning in relation to the catheter, or may comprise a distal cam action on the catheter shaft. Suction or another tissue holding mechanism is preferably employed with a rotating blade to hold the tissue in place while the cut is completed.

In other embodiments the cutter may be triangular in shape, square, or another polygonal shape such as an octagon, such that when forced through the tissue 30 the shaped blade 16 creates an aperture by cutting out an area of the tissue creating a hole, preferably a shaped hole. Notably, the shape of the hole may not match the blade precisely, e.g., an octagonal blade may create a circular hole, and tenting as described herein may substantially alter the shape of the hole.

Figure 1A:
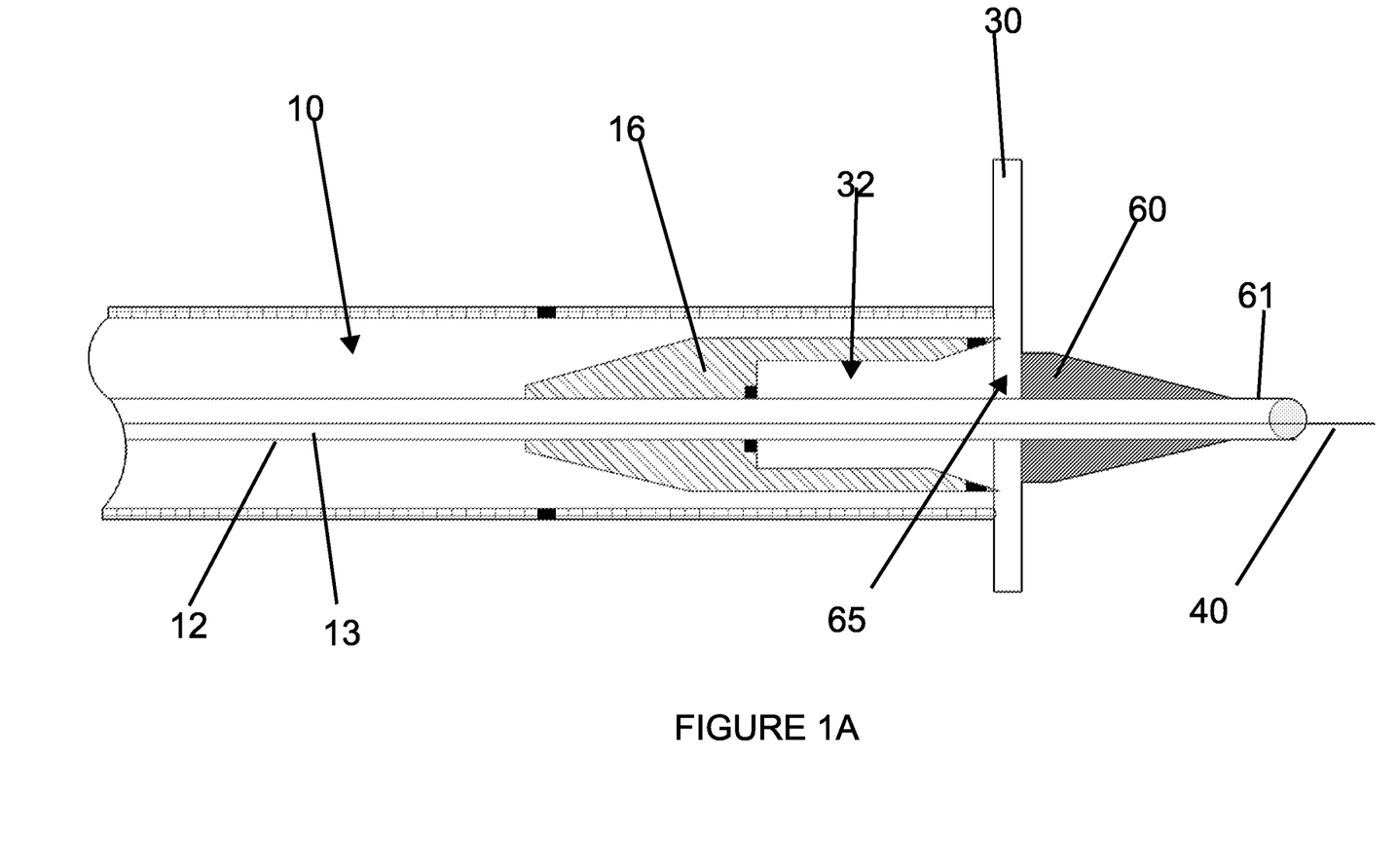
FIG. 1A is a partial perspective view of a catheter and a retention mechanism inserted into a target tissue.

As shown in FIG. 1A catheter 10 includes shaft 12, lumen 13, distal lumen 32 cutting blade 16 as well as a tissue articulator 60, shown in a conical shape. Tissue articulator 60 is actuateable along the lumen 13. The tissue articulator 60 may be actuated for one of a couple purposes, including grabbing tissue, penetrating tissue, tenting tissue, with the cutting blade 16 cutting tissue, or retaining tissue. The tissue articulator 60 may be actuated multiple times for the same or different purposes. It may, for example, be actuated once to penetrate the septum 30. It (or the blade 16) may then be actuated a third time for cutting.

The actuation may take one of several forms. An actuator on the handle may be used. Likewise, the tissue articulator 60 may ride on a guidewire or a catheter that is slidable relative to catheter 10 or cutting means 16. In such a case the actuator is the catheter shaft and it may be slid back and forth as needed.

The tapered cone 60 in one embodiment is the tissue articulator 60, and is attached to a stainless steel tube 61 that comprises the outer diameter of lumen 13. The tapered cone 60 and the cutting blade 16 are both of a sufficient diameter to cut an aperture of the desired size. For example at its widest point the tapered cone 60 may be 6 mm wide. In operation the tapered cone 60 rides over a guidewire 40 that runs through a lumen 13 to the left atrium. The tapered cone 60 is forced through the atrial septum 30. As the tissue in the septum is elastic it will stretch over the tapered cone as it passes through and then will partially recover to fit in the space 65 between the tapered cone 60 and the cutting blade 16. While the space 65 may be a longer space, which may allow for more tissue to be gathered into lumen 32, in one embodiment space 65 is a short narrow segment that only leaves enough of a longitudinal gap for the tissue 30 to fit between the distal tip of the cutting blade 16 and the cone 60, e.g., 2 mm. The tapered cone 60 is then actuated and pulled proximally into the lumen 32. Because the tapered cone 60 fits precisely within the lumen 32 it pulls into the lumen even if the catheter is at an angle or is bent. This action pulls the tissue 30 into the cutting blade 16, cutting an aperture in the interatrial septum. The tissue 30 is captured within the lumen 32 and held in place by the withdrawn tapered cone 60 and removed from the body.

The tapered cone 60 may have a drug coating for one or more purposes. For example, it may have a hydrophilic coating to reduce tearing as it passes through the interatrial septum 30. A slippery tapered cone 60 will reduce tenting due to friction as it passes through the tissue it likewise the tapered cone 60 may have a drug coating that will slow fibroblast proliferation and migration as well as the secretion of extracellular matrices, e.g. Pacelitaxel. Likewise, the cutting blade 16 may include one or more of these coatings.

Figure 2:
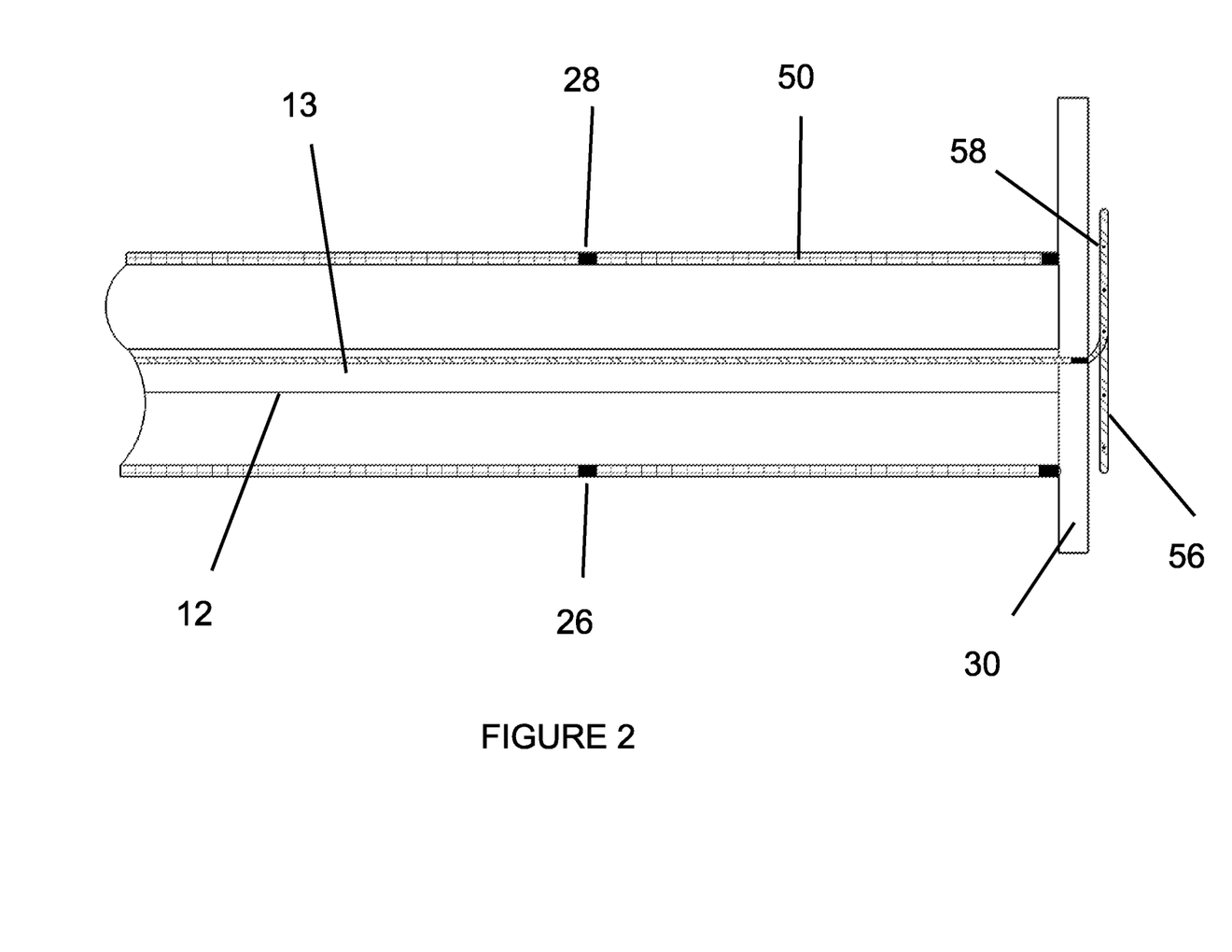
FIG. 2 is a partial perspective view of a catheter constructed according to the present disclosure.

As shown in FIG. 2, in another embodiment cutter 56 is formed of a shape memory metal so that when it is fully retracted and inside catheter 10 it takes a more linear shape. However, when cutter 56 exits the catheter it assumes one of a number shape of shapes. For instance in a first embodiment cutter 56 exits the catheter 10 and assumes a circular shape that is orthogonal to catheter 10, as shown in FIG. 2. Thus when pressed against the tissue from the distal side (from the left atrium) the cutter 56 forms a circular loop against the tissue and cuts a circular hole. Cutter 56 may retain a straight shape while on the proximal side of the interatrial septum, and may be forced through the septum where it assumes a circular shape on the distal side of the septum. It is pulled back against the tissue cutting the aperture. As can be appreciated, once the hole is cut, the blade 56 may be pulled back into the catheter 10 and removed from the heart. The catheter 10 may have irrigation or suction ports 58 on the cutter 56. Cutter 56 may cut from either side of the tissue 30, the proximal or distal side. As may be appreciated, cutter 56 may be a shaped blade in a number of different shapes, including a star, circle, square, triangle, or another polygon.

Figure 3:
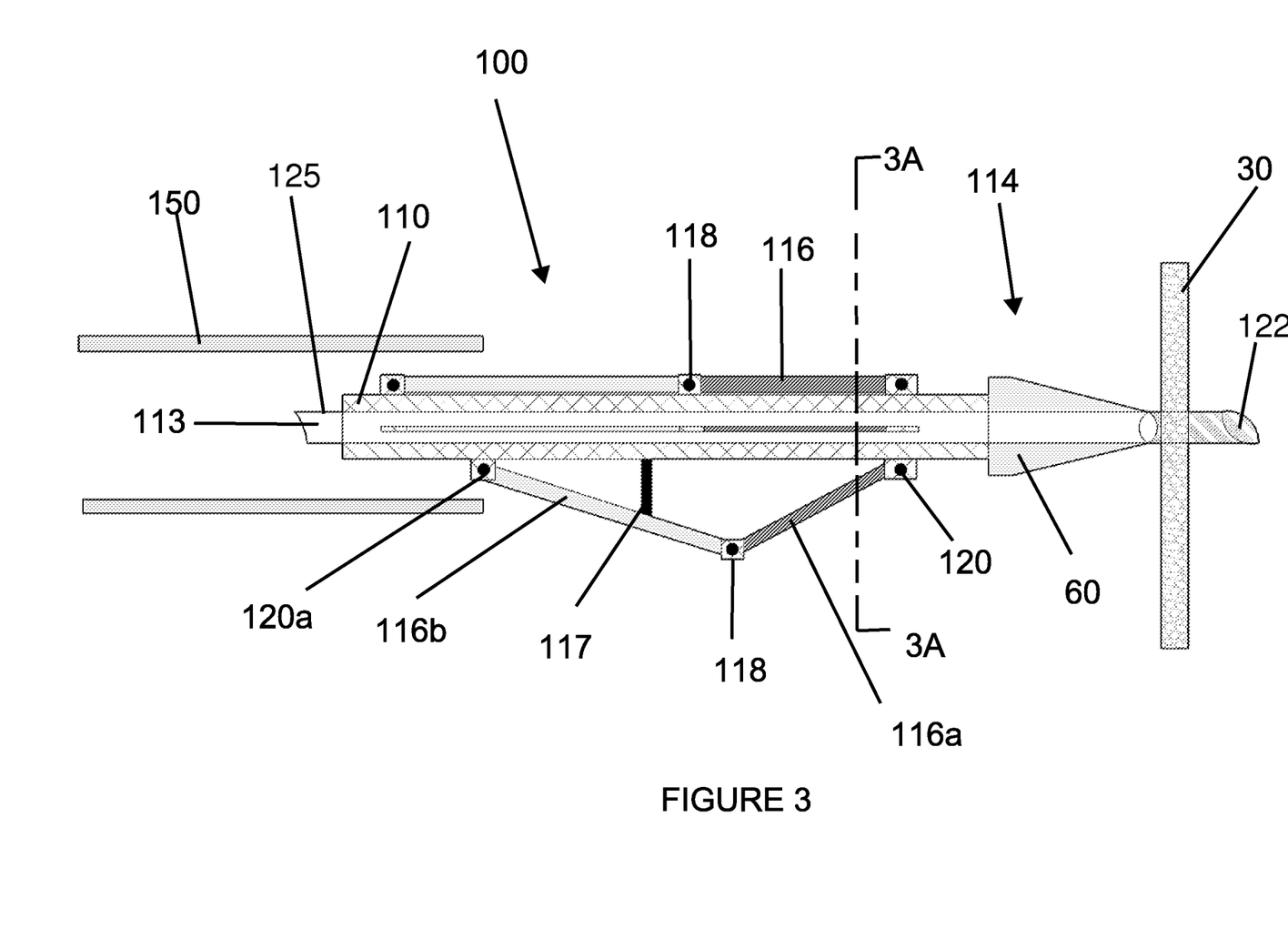
FIG. 3 is a partial perspective view of a catheter constructed according to the present disclosure.
Figure 3A:
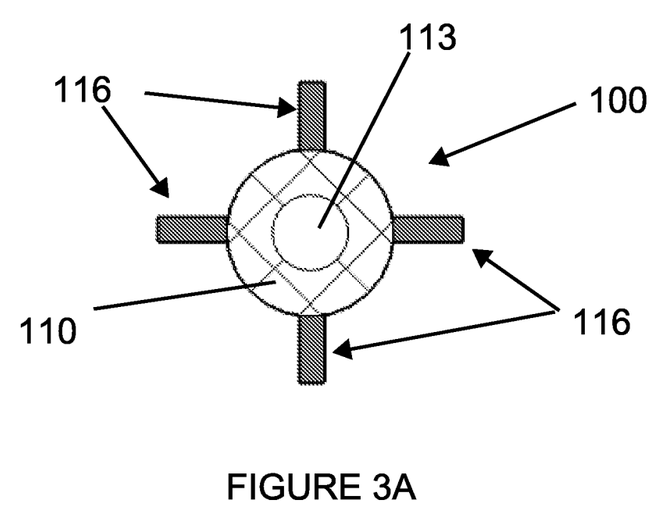
FIG. 3a is a cross sectional view of the catheter of FIG. 3 taken along line 3A on FIG. 3.

While in the first embodiment catheter 10 creates a circular aperture in the interatrial septum, in an alternative embodiment, as shown in FIG. 3, catheter 100 is designed to create a patterned cut in tissue 30 that will provide a durable aperture between the two atria. In particular catheter 100 comprises shaft 110 with a distal end 114. The distal end 114 comprises blades 116. As shown in FIG. 3a, a cross-section of the distal end of the catheter 100 of FIG. 3, the distal end 114 of catheter shaft 110 may comprise four blades 116 arranged approximately 90° apart around the circumference of the catheter 100.

In use, the catheter 100 is inserted into the right atrium while inside sheath 150. Sheath 150 protects the surrounding vein and other tissue from blades 116 until the catheter 100 is in place to create the aperture. There are two broad mechanisms of action. First when catheter 100 is placed against the interatrial septum tissue 30 the introducer 150 may be actuated and withdrawn allowing blades 116 to open. At this point the catheter 100 is actuated or pushed through the interatrial septum 30 and the blades 116 create a patterned cut in the tissue. In the case of four blades the pattern cut appears as an X. The four flaps of tissue that are created will provide a durable aperture.

The physician may also push the introducer 150 up against the interatrial septum 30. The catheter 100 with the blades 116 still retracted may be pushed through the interatrial septum 30. As it passes through the septum, the catheter 100 exits the introducer 150 allowing the blades 116 to deploy. The catheter 100 is then pulled back in a proximal direction towards the right atrium cutting the tissue in the desired pattern. As the catheter 100 is pulled back in the proximal direction and after it has created the desired cut it will reenter the sheath 150 retracting the blades for removal from the body.

It is contemplated that a combination of the two embodiments of FIGS. 1 and 3 is also possible such that a first cutting mechanism 16 will create a hole in the interatrial septum tissue 30 and a second cutting mechanism 116 will create additional cuts and a flap system. The hole and the flaps together to create a durable aperture between the two atria. Likewise, a tapered cone 60 (FIG. 3) may create a small circular hole as it passes through the septum.

With reference to FIG. 3, the blades 116 may be extended by any combination of a biasing arm 117, pivots 118, springs (not shown) or biasing materials such as nitinol. In such a case the blades will typically automatically extend when there are no restrictions on it, e.g., as the catheter exits the catheter sheath or after the catheter has pushed through the interatrial septum to the left atrium. In addition it may be advantageous to have the blades automatically fold in based on contact from one direction and automatically extend when that contact is removed. Thus for example the blades may extend based on contact from a distal side e.g. as the catheter pushes into the interatrial septum the contact with the tissue pushes a distal blade portion 116a in the proximal direction, causing the blade mechanism to swing out from the catheter shaft 110. The blades may then automatically withdraw back into the catheter as the catheter is pulled back through the interatrial septum and the catheter blades are contacted from the proximal side by the tissue, or vice versa. Likewise, a combination of biasing or contact me alternately open or close the blades. For example the blades may be biased to open if there are no restrictions, but may be closed using contact with the tissue or introducer as it is withdrawn.

Likewise the blades 116 may be extended via an actuator on a handle. The blades 116 may be attached via pivot pins 120 to the catheter. The blades 116 may comprise multiple blade sections 116 a and 116 b that pivot around pivots 118, and blade sections 116 a, 116 b, may slide on a slidable pivot pin 120a or may be secured. The blade sections 116 a, 116 b may have equivalent lengths, or may be different.

Even if the blades 116 are designed so that no portion of the tissue is actually removed from the slits as cut, it can be desirable to employ suction through a lumen 113 in the catheter 100 such that any tissue dislodged during the cutting process is safely removed.

While the blades 116 are illustrated with both ends attached to catheter 100, it is equally possible to have only one blade end attached to the catheter 100 and the other end effectively free or biased into position by arm 117, a spring, or a biased construction.

While four blades are pictured, it is within the scope of this embodiment to use other numbers of blades. In particular three blades to five blades would provide a similar result.

Likewise, a catheter with two blades could be utilized to provide a first cut along one axis and then be rotated 90° to provide a second cut along a second axis. Thus after the two cuts a similar X shaped incision in the transatrial septum would be provided. Similarly a catheter with a single blade could be utilized to provide four cuts 90° apart each and again provide an X shaped incision. As can be seen the desired cut pattern can be created by either providing a catheter with blades pre-existing in the desired pattern, or by providing multiple cuts with one or more blades. While embodiments above have been described with catheter blades equidistant from each other, it is also contemplated that the catheter blades 116 may be arranged in a non-equidistant pattern around the catheter if in the judgment of physician a different pattern is preferred.

Blades 116 can be provided in a number of different shapes. For example catheter 100 could have two diamond shaped blades (not shown) on its distal end. The blades can be permanently diamond shaped or could be collapsible. In the event the blades are parallel to each other and on opposite sides of the catheter the incision in the interatrial septum will resemble an H with a hole at the middle (the hole being caused by the catheter itself). Other shapes are also possible. For example the blades could angle towards each other at the top of the catheter and away from each other at the bottom such that the incision in the interatrial septum will resemble in A with a hole in the middle.

Likewise catheter 100 may include a semicircular shaped blade (not shown). In particular the catheter 100 includes a hollow lumen at its distal end. The cutting blade 116 comprises a semicircular shaped blade that can be rotated. In operation the blade is rotated or extended out of the catheter. The cutting blade 116 is then rotated to cut a circular hole in the interatrial septum. The cutting blade 116 is then rotated back into the lumen in catheter 100.

The catheter 100 may further comprise a stainless steel tube 125 with a BRK or other needle 122 on the end for piercing the interatrial septum 30. The stainless steel tube 125 may be actuated manually or via an actuator on handle to pierce the interatrial septum. Once across it is possible to use a tissue articulator such as cone 60 to increase the diameter of the hole or to work in combination with the cutting blades 116 to hold the tissue in place.

In a similar embodiment, cutting blades 116 comprise a swing or support arm at the distal end of the catheter 100. When the catheter exits a sheath, or when the swing arm is actuated for release, the swing arm will rotate from being parallel to the longitudinal axis of the catheter to an orthogonal position. A razor wire is connected between the extended support arm and the body of the catheter 110 proximally of the distal end where the swing arm is attached. As the catheter is pulled back through the tissue the razor wire will create an incision in the tissue. As can be contemplated, as above multiple cutting blades 116 utilizing a razor wire are possible, and specifically four razor wire support arm combinations would create a similar X pattern incision in tissue 30.

Figure 3B:
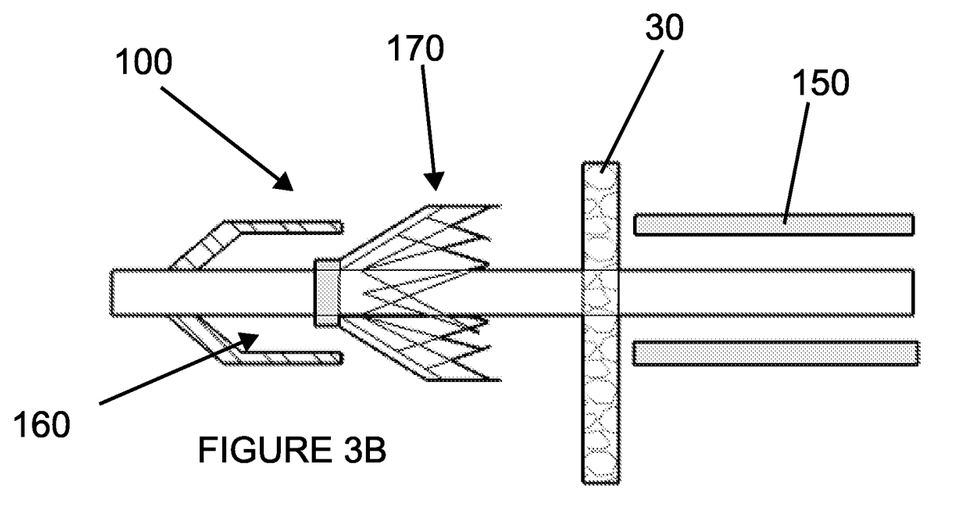
FIG. 3B is a partial perspective view of a catheter constructed according to the present disclosure.

With reference to FIG. 3B, in a further embodiment catheter 100 is pushed through the interatrial septum 30 to the distal side. Catheter 100 includes a lumen 160. Lumen 160 is closed in the distal direction as shown, but is open in the proximal direction. Nestled within lumen 160 is a nitinol basket. Upon actuation the nitinol basket 170 is withdrawn proximally. In a first embodiment, as the nitinol basket 170 exits the lumen 160 it expands substantially forming a much wider basket. The proximal edges of the basket are sharp and accordingly may be drawn into and through the tissue both cutting the tissue to create the aperture, and retaining the tissue for removal. After the aperture is created, the catheter is actuated a second time and the nitinol cutter 170 is pushed back into the lumen 160 causing it to close back up for removal from the body.

In a second embodiment, as the nitinol basket 170 exits the lumen 160 it expands substantially forming a much wider basket to serve as a tissue articulator to retain the tissue or to hold the tissue into a cutting means. As depicted, the proximal edges of the basket may be sharp and accordingly may be drawn into the tissue to hold it and bias it into the cutting means (not shown). The basket 170 may also lack sharp edges and may simply bias or retain the tissue, for example forming a spherical basket 170. After the aperture is created, the catheter is actuated a second time and the nitinol basket 170 is pushed back into the lumen 160 causing it to close back up for removal from the body.

Figure 4:
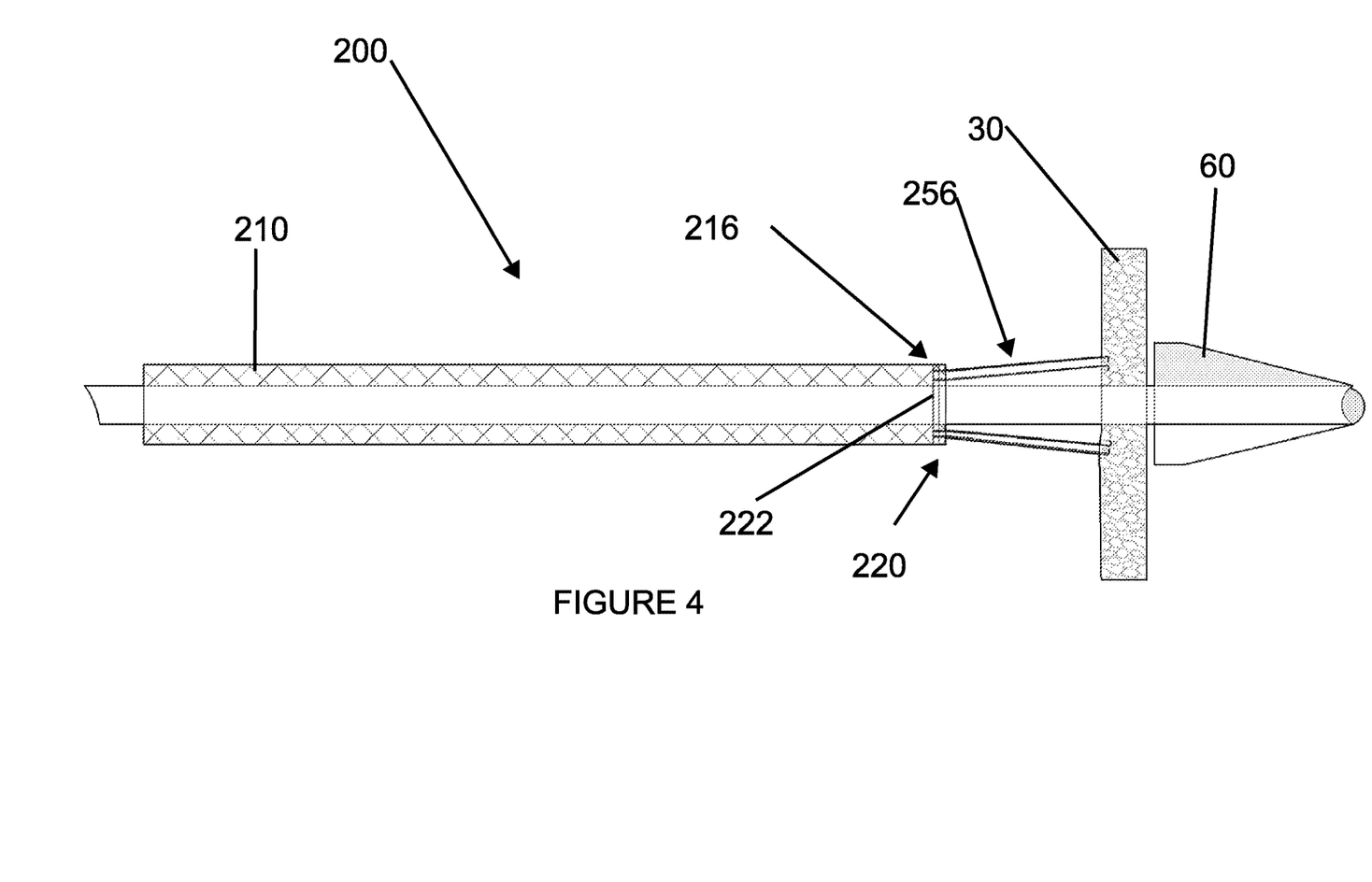
FIG. 4 is a partial perspective view of a catheter constructed according to the present disclosure.

Referring to FIG. 4, in another embodiment of the catheter 200, the catheter 200 comprises an elongated hollow catheter shaft 210 having an interior lumen in which one or more hooks 256 are positioned. The catheter 200 further comprises a distal end 220 with a lumen 222. The hooks 256 are extended out of the catheter shaft 210 and lumen 222 and into the tissue of the interatrial septum 30. Once the hooks 256 firmly grasp the tissue, the hooks 256 are drawn back into lumen 222 to positively retain the tissue 30. While four hooks are shown in FIG. 4, the number of hooks may vary and in particular embodiments with one hook to four hooks are contemplated.

As shown in FIG. 4, when the tissue 30 is grasped by hooks 256 and withdrawn into the lumen 222 the cutting device 216 may be employed to cut the aperture into the tented tissue 30. FIG. 4 depicts the hooks 256 as orienting towards the center of the catheter's central axis. However it is also contemplated that the hooks may be oriented away from the axis of the catheter in another embodiment. Likewise hooks 256 are shown as a long thin rod with a short hook on the end. However, in another embodiment the two hooks more resemble the long grasping arms of a sturdy pliers.

Figure 5:
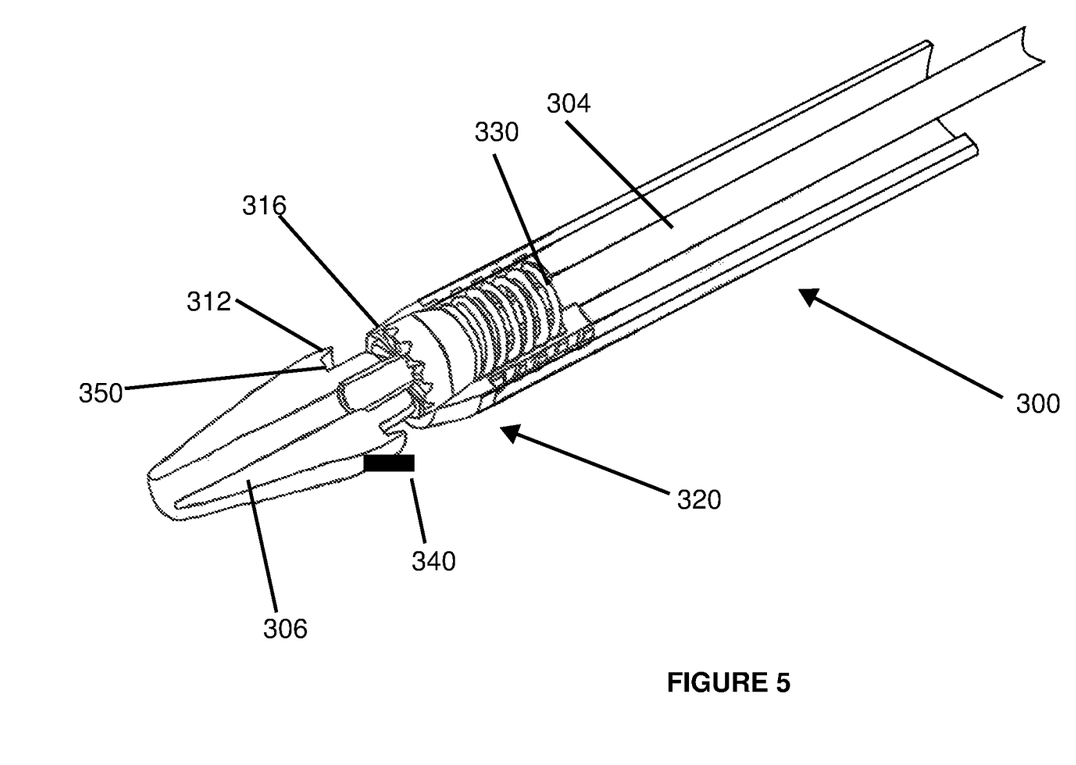
FIG. 5 is a cutaway partial perspective view of a catheter constructed according to the present disclosure.

In a further embodiment, illustrated in FIG. 5, the catheter 300 comprises an elongated hollow catheter 300 having a lumen 304 in which a hooking device 306 is positioned. The catheter further comprises a distal end 320 and a blade 316. The hooking device 306 has barbs 312 that are used to grab or hook into the interatrial septum. The hooking device 306 is used pull the septum toward the blade 316 to cut an aperture in the septum. The blade 316 may be actuated or pushed through tissue 30 via spring 330. As with above embodiments, the hooking device 306 may retract inside a cutting blade 316. However, as depicted in FIG. 5, the hooking device may ride over the outside of cutting device 316, e.g., by barbs 312 riding over the outside of cutting blade 316, and cutting blade 316 sitting flush inside the barbs or the cone 306.

Hooking device 306 may include self-expanding arms 340 or portions that may, once the hooking device is passed through the target tissue 30, expand to grab a wider portion of tissue 30. Such an arrangement allows the hooking device to begin as a smaller diameter device that will more easily navigate through the veins to the interatrial septum, but then be expanded to a larger device that will attach to a larger segment of the interatrial septum to create a larger aperture.

The hooking device 306 may operate in different manners. First, it may merely penetrate into but not through the tissue and via teeth pull the tissue into the lumen 304 of the catheter 300. Preferably however a conically shaped hooking device 306 penetrates through the septum entirely, and is withdrawn back to the tissue such that its proximal face 350 grabs the tissue and pulls it into the lumen of the catheter 300. At this point the tissue is brought in contact with the cutting device 316. The cutting device 316 may comprise a shaped cutting device as disclosed above. In addition cutting device 316 may comprise a semicircular blade. The semicircular blade 316 may be rotated such that as it is rotated it will create a circular hole in the tissue. The advantage of a semicircular blade over a fully circular blade is that less force will be required for the cutting action. The disadvantage is that the blade must be rotated, or the entire catheter be rotated, to create the desired cut. In the event the physician does not wish to remove tissue from the interatrial septum a semicircular blade may be utilized to create a flap by not rotating 360°.

While FIG. 5 shows the cutting device 316 on the distal portion of the catheter shaft 300, the cutting device 316 may instead be on the proximal portion of hooking device 306. Likewise there may be two cutting devices 316: one on the distal end of the catheter shaft 300, and one on the proximal portion of the hooking device 306. As they are drawn together they will cut the tissue via a scissoring action.

Figure 6:
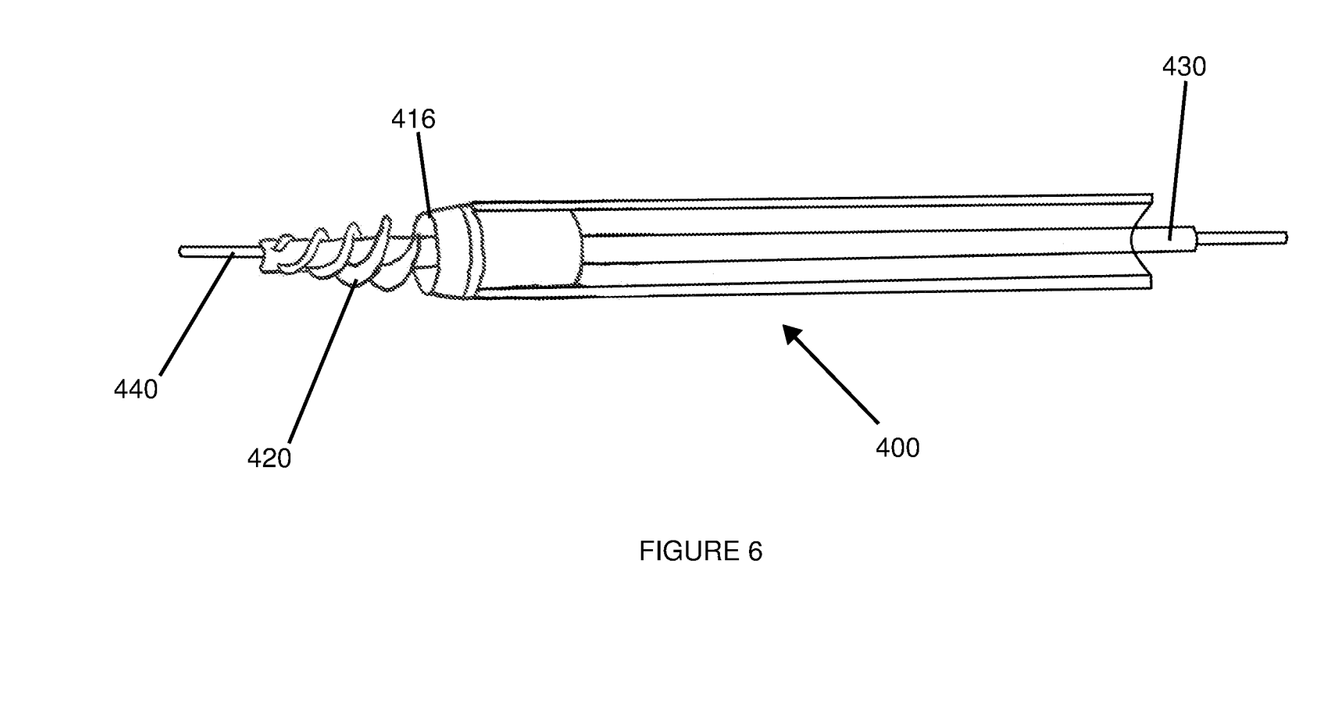
FIG. 6 is a partial perspective view of a catheter constructed according to the present disclosure.

With reference to FIG. 6 the catheter 400 may comprise an auger 420. The auger 420 may include a lumen 430 for riding over a guidewire 440. In use the guidewire 440 crosses the septum into the left atrium. The auger 420 is rotated to likewise cross the septum. Because of the spiral design of the auger it does not create as large of a tear or perforation in the septum 30 because only one radius of the auger is in contact with the septum at any given time. However once the auger is in the left atrium, it may be pulled back to pull the septum 30 into cutter 416.

Figure 7:
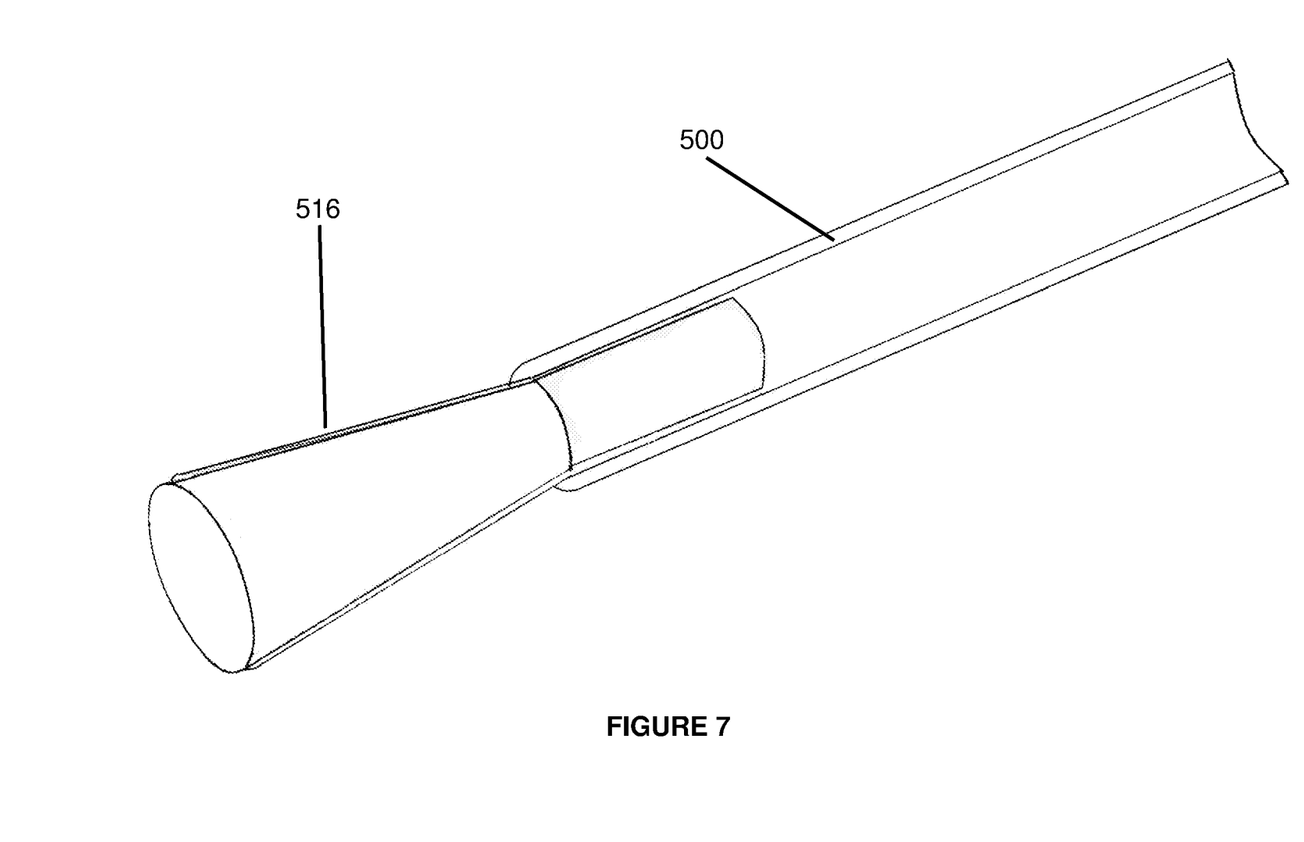
FIG. 7 is a partial perspective view of a catheter constructed according to the present disclosure.

The cutting device may take alternative forms. Similar to the semicircular blade, the blade may take the form of a coiled blade (not shown). The coiled blade may be contained within the lumen of the catheter. Once deployed out of the catheter and uncoiled the blade is used to cut a hole in the septum as above. The coil may take several forms. For instance the coiled blade may take the form of an auger (not shown). Likewise the coiled blade may take the form of a coiled rolled sheet as shown in FIG. 7. Both such forms may give the physician discretion as to how large of an aperture he wishes to create in the interatrial septum. For instance a blade formed into a coiled rolled sheet 516 may, as it exits the catheter further and further, continually take on a larger and larger diameter. Thus for a small aperture the physician may only extend the coiled rolled sheet a short distance out of the catheter 500 and as such the coiled rolled sheet will only create a aperture approximately the diameter of the catheter itself. However if a larger aperture is desired the coiled rolled sheet will be removed further and further out of the catheter as shown in FIG. 7 and allowed to unroll into a larger circular shape. Thus the created aperture will be much larger. In one embodiment suction is employed with the coiled rolled sheet to hold the tissue in place.

While FIG. 7 depicts the coiled rolled sheet 516 as exiting the catheter 500, it is contemplated that the coiled rolled sheet may be coiled around the exterior of catheter 500, and may unfurl as it exits an introducer (not shown).

Because the coiled rolled sheet is capable of creating different sized apertures, it is possible for the physician to provide a progressive enlargement of the aperture during the procedure. For example the physician can create a first aperture at a first size, monitor the ejection fraction for example, or the pressure in the two atria, and determine that a larger aperture is required. The physician would then adapt the size of the cutting mechanism and create a second, larger aperture in the same place as the first aperture was. In the alternative, the physician could simply create a first aperture in a second location that is substantially the same size as the first aperture using the original size cutting means.

Figure 8:
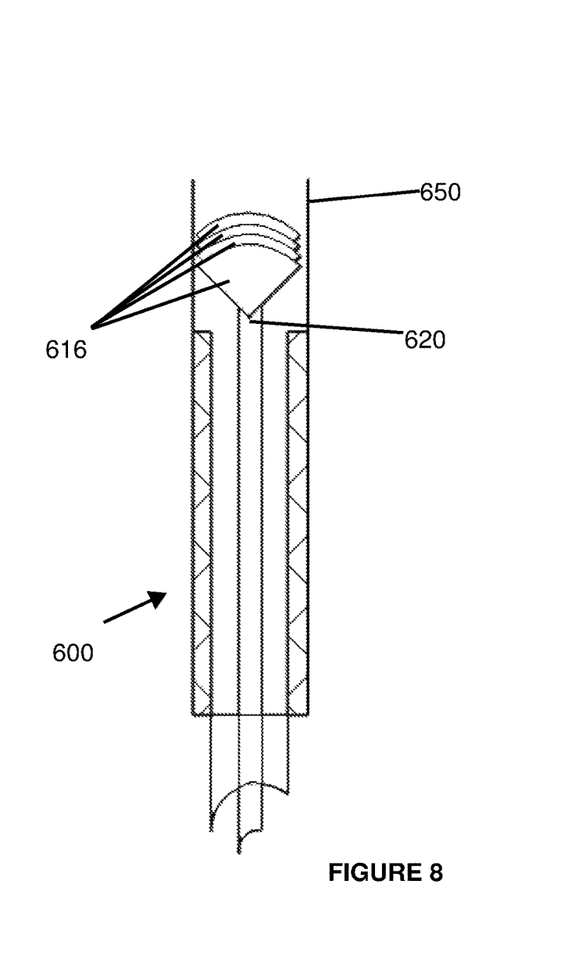
FIG. 8 is a partial perspective view of a catheter constructed according to the present disclosure.
Figure 8A:
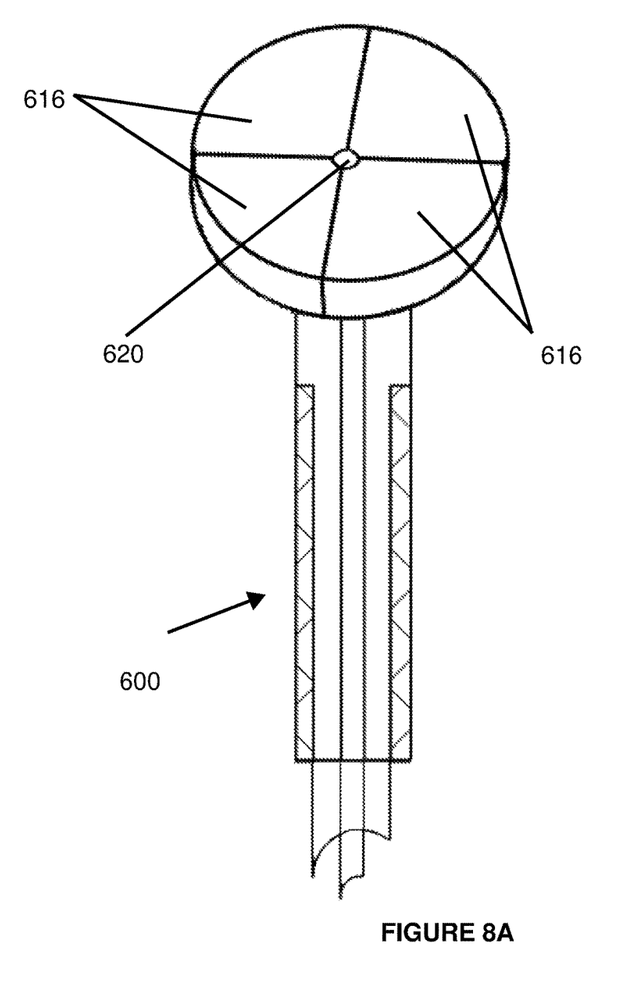
FIG. 8A is a partial perspective view of a catheter constructed according to the present disclosure.

With reference to FIGS. 8 and 8a, the catheter 600 may comprise multiple angled cutting arms 616. Each cutting arm is attached to the catheter shaft 610 by via a hinge 620. While the cutting arms 616 remain within the sheath 650 they are aligned with each other to present a smaller cross-section. However once deployed out of the sheath they rotate on the hinge to form an overlapping cutting surface in a desired shape, e.g., a circular shape as shown in FIG. 8a. While the multiple cutting arms 616 are depicted in a leaf shape that opens into the four quarters of a circle, the cutting arms 616 may take multiple forms. For example while the cutting arms are depicted as being oriented perpendicularly to the longitudinal axis of catheter 600, the cutting arms 616 may be oriented parallel to the longitudinal axis of catheter 600, and as such when open would present a similar cutting edge to the coiled rolled sheet 516 depicted in FIG. 7.

The invention claimed is:

1. A method of treating congestive heart failure comprising the steps of:
   inserting a catheter into the right atrium of the heart, the catheter comprising:
      a shaft,
      a shaped cutting blade arranged around a distal catheter portion,
      a tissue articulator, the tissue articulator having a first position and a second position,
      an actuator connected to the tissue articulator,
   crossing the interatrial septum,
   actuating the actuator to move the tissue articulator into the second position that holds a tissue for the shaped cutting blade,
   cutting an aperture in the interatrial septum between the right atrium and the left atrium,
   removing a cut tissue from the right atrium.

2. The method of claim 1 further comprising a step of attaching a tissue removal device to the interatrial septum.

3. The method of claim 2, further comprising the step of actuating the tissue removal device to remove the cut tissue.

4. The method of claim 3, wherein the tissue removal device comprises a hook, a balloon, a disk, or an expandable basket.

5. The method of claim 4, further comprising the step of tenting the tissue using the tissue removal device to pull, grasp, or push the tissue into a catheter lumen or the shaped blade before it is cut.

6. The method of claim 2, wherein the tissue removal device comprises a proximal portion and a distal portion, and further comprising the step of actuating the tissue removal device.

7. The method of claim 6, wherein the step of actuating the tissue removal device reduces the distance between the proximal portion and distal portion of the tissue removal device.

8. The method of claim 7, wherein actuating the tissue removal device causes the proximal portion and the distal portion of the tissue removal device to securely hold the tissue between them.

9. The method of claim 6, wherein the removing step comprises the step of withdrawing the tissue removal device into the shaped blade or the catheter with the cut tissue.

10. The method of claim 1, further comprising the step of aligning the tissue and the shaped cutting blade so they are substantially parallel.

11. The method of claim 1 wherein the removing step comprises pulling the cut tissue into a lumen at a distal end of the catheter shaft.

12. The method of claim 1 further comprising a step of expanding the shaped cutting blade to a diameter greater than the diameter of the catheter.

13. The method of claim 1, further comprising a step of applying suction to the tissue.

14. The method of claim 1, further comprising the step of tenting the tissue so that a larger portion of the tissue may be cut in the cutting step.

15. The method of claim 14, wherein the tissue articulator is a tapered cone having a proximal face, and the tenting step uses the proximal face to pull the tissue into the catheter to tent the tissue.

16. The method of claim 1, further comprising the step of locating a radiopaque marker on the catheter.

17. The method of claim 16, further comprising the steps of inserting the catheter in a sheath, navigating the sheath to the heart, and advancing a distal part of the catheter out of the sheath.

18. The method of claim 17, further comprising the step of locating a radiopaque marker on the sheath.

* * * * *